United States Patent
Karin et al.

(10) Patent No.: US 9,670,282 B2
(45) Date of Patent: *Jun. 6, 2017

(54) COMPOSITIONS AND METHODS FOR DIAGNOSING AND TREATING AN INFLAMMATION

(71) Applicant: RAPPAPORT FAMILY INSTITUTE FOR RESEARCH IN THE MEDICAL SCIENCES, Haifa (IL)

(72) Inventors: Nathan Karin, Haifa (IL); Rachel Anunu, Haifa (IL); Gizi Wildbaum, Kiryat Yam (IL); Yaniv Zohar, Kiryat Tiv'on (IL); Nir Netzer, Mazkeret Batia (IL)

(73) Assignee: RAPPORT FAMILY INSTITUTE FOR RESEARCH IN THE MEDICAL SCIENCES, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,460

(22) Filed: May 18, 2016

(65) Prior Publication Data

US 2016/0280785 A1    Sep. 29, 2016

Related U.S. Application Data

(60) Continuation of application No. 14/828,615, filed on Aug. 18, 2015, now Pat. No. 9,371,385, which is a continuation of application No. 13/913,587, filed on Jun. 10, 2013, now Pat. No. 9,145,460, which is a division of application No. 11/991,711, filed as application No. PCT/IL2006/001059 on Sep. 11, 2006, now Pat. No. 8,512,698, which is a continuation-in-part of application No. 11/222,745, filed on Sep. 12, 2005, now Pat. No. 8,017,113.

(51) Int. Cl.
| | |
|---|---|
| *A61K 38/00* | (2006.01) |
| *A61K 39/00* | (2006.01) |
| *A61K 39/395* | (2006.01) |
| *C07K 16/28* | (2006.01) |
| *G01N 33/68* | (2006.01) |

(52) U.S. Cl.
CPC ........ *C07K 16/28* (2013.01); *A61K 39/3955* (2013.01); *C07K 16/2896* (2013.01); *G01N 33/6893* (2013.01); *A61K 2039/505* (2013.01); *C07K 2317/21* (2013.01); *C07K 2317/565* (2013.01); *C07K 2317/567* (2013.01); *C07K 2317/76* (2013.01); *G01N 2333/70596* (2013.01); *G01N 2800/065* (2013.01); *G01N 2800/202* (2013.01)

(58) Field of Classification Search
None
See application file for complete search history.

(56) References Cited

U.S. PATENT DOCUMENTS

| | | | |
|---|---|---|---|
| 8,409,569 B2 * | 4/2013 | Karin | C07K 16/28 424/130.1 |
| 9,145,460 B2 | 9/2015 | Karin et al. | |

OTHER PUBLICATIONS

Mariuzza, R.A. et al. 'The Structural Basis of Antigen-Antibody Recognition' Annu. Rev. Biophys. Biphys. Chem. 16:139-159, 1987.*
Rudikoff et al. "Single Amino Acid Substitution Altering Antigen-Binding Specificity" PNAS. 79:1979-1983, 1982.*
Rader et al. PNAS. 95:8910-8915, 1998.*
Tyndall et al. 'Chronic GVHD as an autoimmune disease.' Best Practice & Research Clinical Haematology vol. 21 , No. 1, pp. 281-289, 2008.
US Office Action for U.S. Appl. No. 14/828,615 dated Oct. 2, 2015.

* cited by examiner

*Primary Examiner* — Nora Rooney
(74) *Attorney, Agent, or Firm* — Pearl Cohen Zedek Latzer Baratz LLP

(57) ABSTRACT

A method of treating multiple sclerosis (MS) in a subject in need thereof, the method comprising administering to said subject a therapeutically effective amount of an isolated polypeptide comprising an antigen recognition domain capable of specifically binding a human scavenger receptor, wherein said antigen recognition domain comprises CDR amino acid sequences as set forth in SEQ ID NO: 11, 15, 19, 23, 27 and 31, thereby treating MS in the subject.

1 Claim, 8 Drawing Sheets

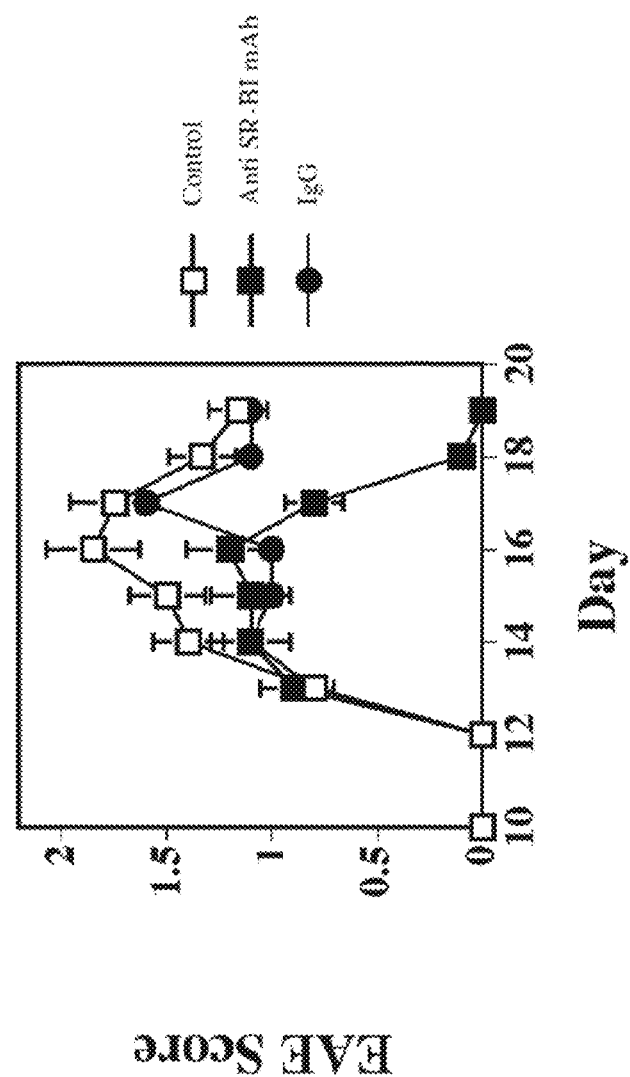

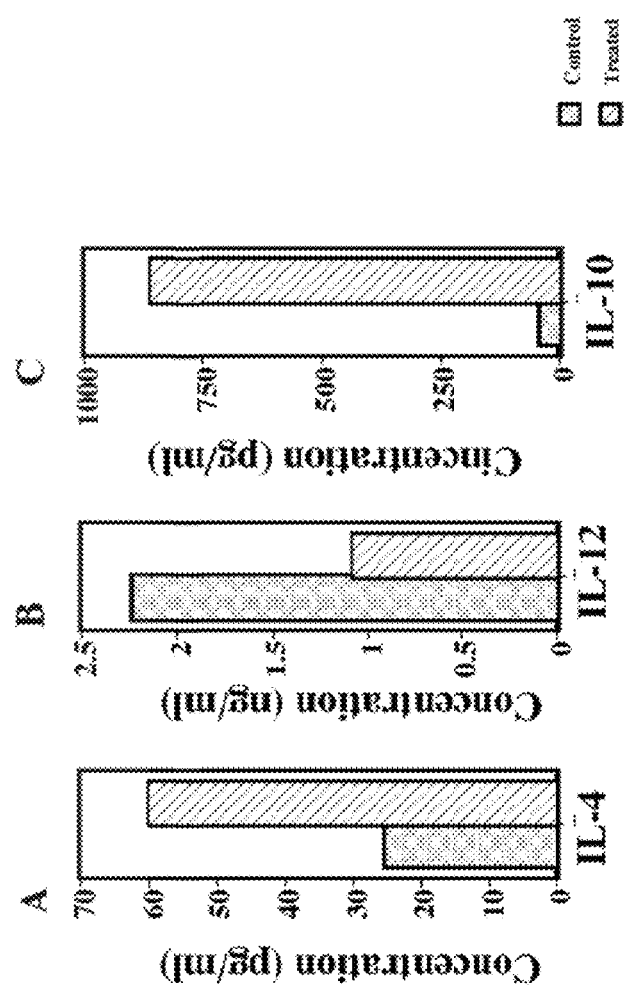
Figs. 5a-c

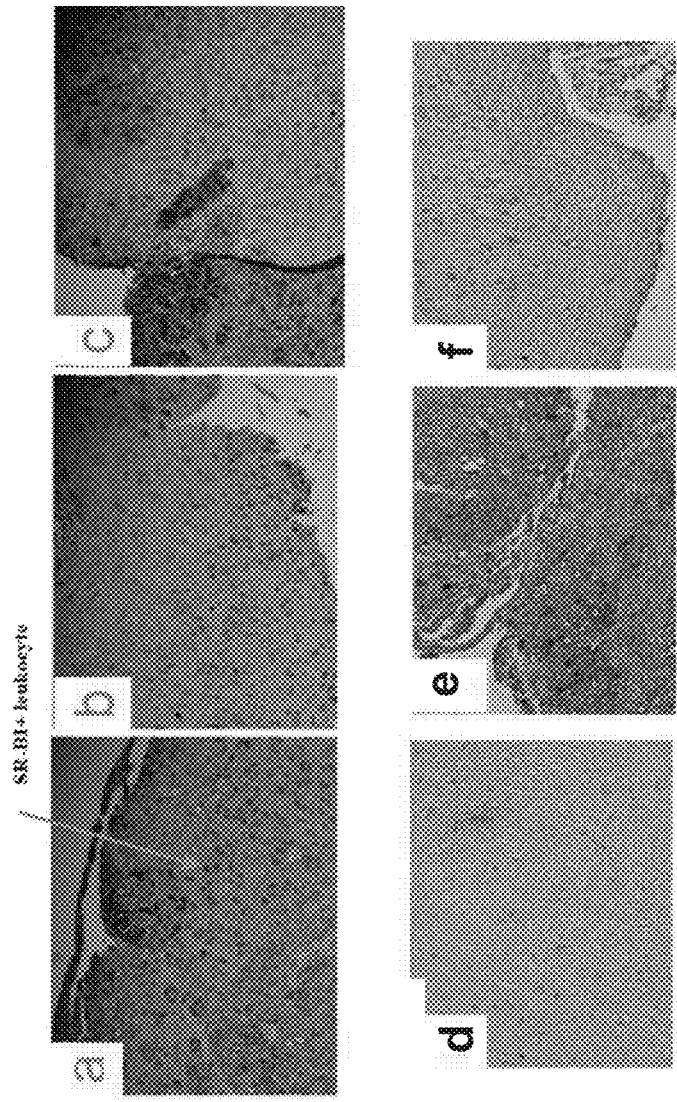
Figs. 6a-f

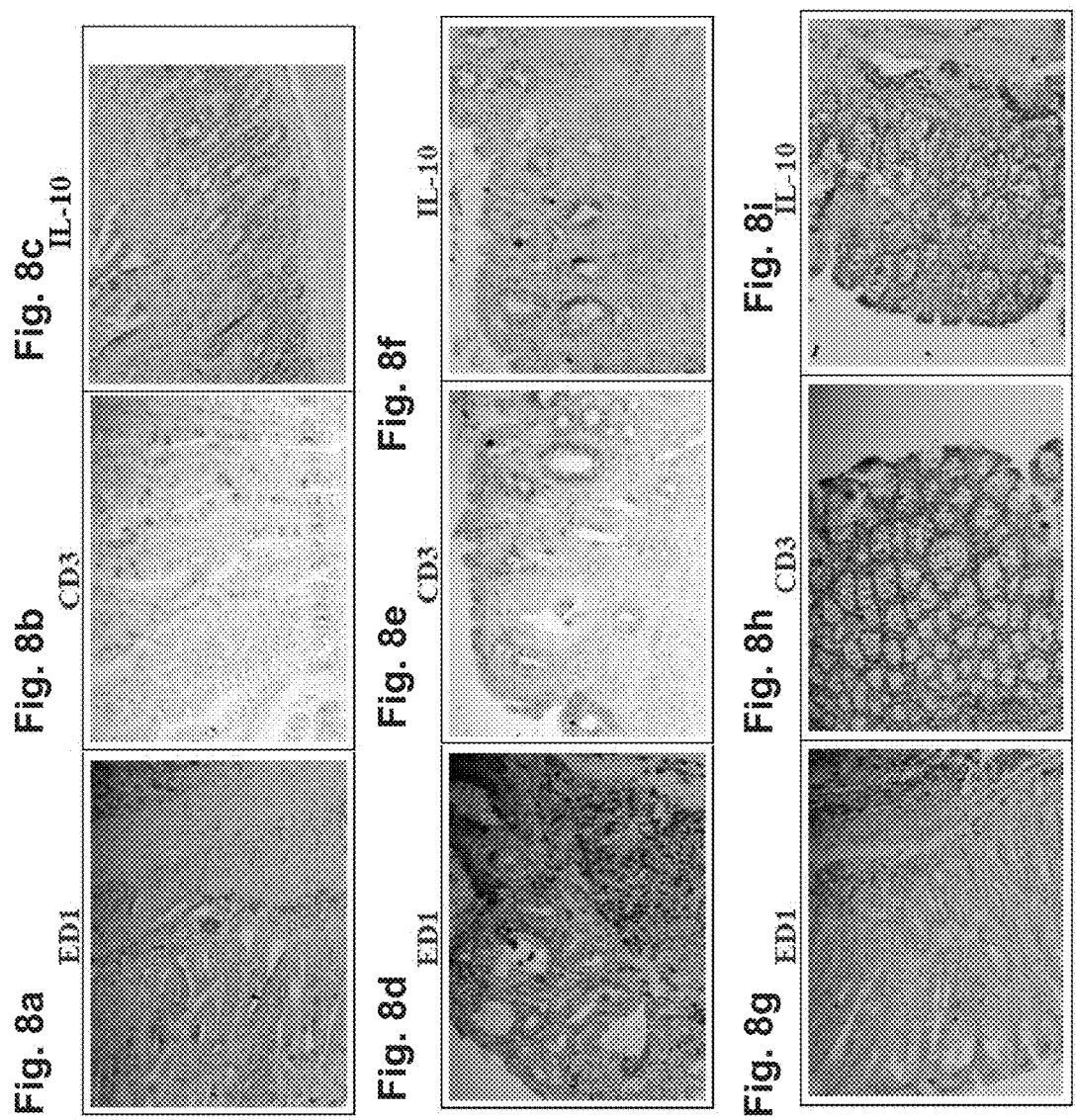

SEQUENCE LISTING

```
<160> NUMBER OF SEQ ID NOS: 32

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
ccatgggcgg cagctccagg gc                                            22

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
ctacagcttg gcttcttgca c                                             21

<210> SEQ ID NO 3
<211> LENGTH: 1531
<212> TYPE: DNA
<213> ORGANISM: Homo sapiens

<400> SEQUENCE: 3
catgggcggc agctccaggg cacgctgggt ggccttgggg ctgggcgttc tagggctgct    60
gtgtgctgcg ctcggcgtta tcgtgattct catggtgccc tcgctcatca acagcaggt    120 gctcaagaat gtccgcatag accccagcag cctgtccttt gggatgtgga aggagatccc    180
tgttcccttc tacttgtccg tctacttctt cgaggtggtc aaccccagcg aggtcctaaa    240
tggccagaag ccagtagtcc gggagcgcgg accctatgtc tacagggagt tcagacaaaa    300
ggttaacatc accttcaatg acaatgacac ggtgtcctac atagagaacc gaagccttca    360
tttccagcca gacaggtccc agggctcaga gagtgactac attgtactgc ctaacatcct    420
ggtcctggga gggcagtga tgatggagga caagcccaca agcctgaagc tgctaatgac    480 cttgggggttg gtcaccatgg gccagcgggc ctttatgaac cgcacggttg gtgagatcct    540
gtggggctat gaggatccgt tcgtgaattt cctcagcaaa tatttcccag acatgttccc    600
catcaaaggc aaatttggcc tgttcgttgg gatgaaccac tcagagttct ggctcttcac    660
cgtcttacag ggtgtccaga atttcagcaa gatccatctg gtggataagt ggaacggcct    720
cagcgaggtc aaatattggc attcggaaca gtgcaacatg atcaatggta ctgccgggca    780
gatgtgggca ccattcatga cacccgaatc ctcactggaa ttcttcagcc agaagcctg    840 cagatctatg aagctcacct accaggaatc aagggtgttc gaaggcatcc ccacttatcg    900
```

```
cttcacggcc cccgatactt tgtttgccaa cgggtccgtc tacccaccta atgaaggctt    960
ctgcccgtgc cgcgagtccg gcattcagaa tgtcagcacc tgcaggtttg gtgcgcccct   1020
gtttctctcc cagccccact tctacaatgc tgaccccgtg ctgtcagaag ctgttcttgg   1080
tctgaaccct gacccaaggg agcattcttt gttccttgac atccacccgg tcactgggat   1140
ccccatgaac tgttccgtga agatgcagct gagtctgtac atcaaatccg tcaagggcgt   1200
cgggcaaaca gggaagatcg agccagtagt cctgccattg ctgtggttcg aacagagcgg   1260
gatgatgggt ggcaagaccc tgaacacgtt ctacacgcag ctggtgctga tgccccaggt   1320
tcttcactac gcgcagtatg tgctgctggg gcttggaggc ctcctgctgc tggtgcccat   1380
catttaccaa ctgcgcagcc aggagaaatg ctttttattt tggagtggta gtaaaaaggg   1440
ctcgcaggat aaggaggcca tgcaggccta ctctgagtct ctgatgtcac cagctgccaa   1500
gggcacggta gtgcaagaag ccaagctgta g                                  1531

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
atggatgacg atatcgctgc gctc                                            24

<210> SEQ ID NO 5
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 5
ctaccggcca gccagacg                                                   18

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
ccatgggctg ctccgccaaa                                                 20

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7
ctacagtttt gcttcctgca g                                               21

<210> SEQ ID NO 8
<211> LENGTH: 1530
<212> TYPE: DNA
<213> ORGANISM: Homo sapiens

<400> SEQUENCE: 8
atgggctgct ccgccaaagc gcgctgggct gccggggcgc tgggcgtcgc ggggctactg    60
```

-continued

```
tgcgctgtgc tgggcgctgt catgatcgtg atggtgccgt cgctcatcaa gcagcaggtc    120
cttaagaacg tgcgcatcga ccccagtagc ctgtccttca acatgtggaa ggagatccct    180
atccccttct atctctccgt ctacttcttt gacgtcatga accccagcga gatcctgaag    240
ggcgagaagc cgcaggtgcg ggagcgcggg ccctacgtgt acaggagtc caggcacaaa    300
agcaacatca ccttcaacaa caacgacacc gtgtccttcc tcgagtaccg caccttccag    360
ttccagccct ccaagtccca cggctcggag agcgactaca cgtcatgcc caacatcctg    420
gtcttgggtg cggcggtgat gatggagaat aagcccatga ccctgaagct catcatgacc    480
ttggcattca ccaccctcgg cgaacgtgcc ttcatgaacc gcactgtggg tgagatcatg    540
tggggctaca aggaccccct tgtgaatctc atcaacaagt actttccagg catgttcccc    600
ttcaaggaca gttcggatt atttgctgag ctcaacaact ccgactctgg gctcttcacg    660
gtgttcacgg gggtccagaa catcagcagg atccacctcg tggacaagtg aacgggctg    720
agcaaggttg acttctggca ttccgatcag tgcaacatga tcaatggaac ttctgggcaa    780
atgtggccgc ccttcatgac tcctgagtcc tcgctggagt tctacagccc ggaggcctgc    840
cgatccatga agctaatgta caaggagtca ggggtgtttg aaggcatccc cacctatcgc    900
tcgtggctc ccaaaaccct gtttgccaac gggtccatct acccacccaa cgaaggcttc    960
tgcccgtgcc tggagtctgg aattcagaac gtcagcacct gcaggttcag tgcccccttg   1020
tttctctccc atcctcactt cctcaacgcc gacccggttc tggcagaagc ggtgactggc   1080
ctgcacccta accaggaggc acactccttg ttcctggaca tccacccggt cacgggaatc   1140
cccatgaact gctctgtgaa actgcagctg agcctctaca tgaaatctgt cgcaggcatt   1200
ggacaaactg ggaagattga gcctgtggtc ctgccgctgc tctggttgc agagagcggg   1260
gccatggagg gggagactct tcacacattc tacactcagc tggtgttgat gcccaaggtg   1320
atgcactatg cccagtacgt cctcctggcg ctgggctgcg tcctgctgct ggtccctgtc   1380
atctgccaaa tccggagcca agagaaatgc tatttattt ggagtagtag taaaaagggc   1440
tcaaaggata aggaggccat tcaggcctat tctgaatccc tgatgacatc agctcccaag   1500
ggctctgtgc tgcaggaagc aaaactgtag                                    1530
```

<210> SEQ ID NO 9
<211> LENGTH: 23
<212> TYPE: PRT
<213> ORGANISM: Artificial sequence
<220> FEATURE:
<223> OTHER INFORMATION: FWR1 of E12 light chain

<400> SEQUENCE: 9

Asp Ile Gln Met Thr Gln Thr Thr Ser Ser Leu Ser Ala Ser Leu Gly
1               5                   10                  15
Asp Arg Val Thr Ile Ser Cys
            20

<210> SEQ ID NO 10
<211> LENGTH: 69
<212> TYPE: DNA
<213> ORGANISM: Artificial sequence
<220> FEATURE:
<223> OTHER INFORMATION: FWR1 of E12 light chain

<400> SEQUENCE: 10

```
gatatccaga tgacccagac tacatcctcc ctgtctgcct ctctgggaga cagagtcacc    60
```

```
atcagttgc                                                              69

<210> SEQ ID NO 11
<211> LENGTH: 11
<212> TYPE: PRT
<213> ORGANISM: Artificial sequence
<220> FEATURE:
<223> OTHER INFORMATION: CDR1 of E12 light chain

<400> SEQUENCE: 11

Ser Ala Ser Gln Gly Ile Ser Asn Tyr Leu Asn
1               5                   10

<210> SEQ ID NO 12
<211> LENGTH: 33
<212> TYPE: DNA
<213> ORGANISM: Artificial sequence
<220> FEATURE:
<223> OTHER INFORMATION: CDR1 of E12 light chain

<400> SEQUENCE: 12
agtgcaagtc agggcattag caattattta aac                                   33

<210> SEQ ID NO 13
<211> LENGTH: 15
<212> TYPE: PRT
<213> ORGANISM: Artificial sequence
<220> FEATURE:
<223> OTHER INFORMATION: FWR2 of E12 light chain

<400> SEQUENCE: 13

Trp Tyr Gln Gln Lys Pro Asp Gly Thr Val Lys Leu Leu Ile Tyr
1               5                   10                  15

<210> SEQ ID NO 14
<211> LENGTH: 45
<212> TYPE: DNA
<213> ORGANISM: Artificial sequence
<220> FEATURE:
<223> OTHER INFORMATION: FWR2 of E12 light chain

<400> SEQUENCE: 14
tggtatcagc agaaaccaga tggaactgtt aaactcctga tctat                      45

<210> SEQ ID NO 15
<211> LENGTH: 7
<212> TYPE: PRT
<213> ORGANISM: Artificial sequence
<220> FEATURE:
<223> OTHER INFORMATION: CDR2 of E12 light chain

<400> SEQUENCE: 15

Tyr Thr Ser Ser Leu His Ser
1               5

<210> SEQ ID NO 16
<211> LENGTH: 21
<212> TYPE: DNA
<213> ORGANISM: Artificial sequence
<220> FEATURE:
<223> OTHER INFORMATION: CDR2 of E12 light chain

<400> SEQUENCE: 16
tacacatcaa gtttacactc a                                                21

<210> SEQ ID NO 17
```

<211> LENGTH: 32
<212> TYPE: PRT
<213> ORGANISM: Artificial sequence
<220> FEATURE:
<223> OTHER INFORMATION: FWR3 of E12 light chain

<400> SEQUENCE: 17

Gly Val Pro Ser Arg Phe Ser Gly Ser Gly Ser Gly Thr Asp Tyr Ser
1               5                   10                  15

Leu Thr Ile Asn Asn Leu Glu Pro Glu Asp Ile Ala Thr Tyr Tyr Cys
            20                  25                  30

<210> SEQ ID NO 18
<211> LENGTH: 96
<212> TYPE: DNA
<213> ORGANISM: Artificial sequence
<220> FEATURE:
<223> OTHER INFORMATION: FWR3 of E12 light chain

<400> SEQUENCE: 18
ggagtcccat caaggttcag tggcagtggg tctgggacag attattctct caccatcaac      60
aacctggaac ctgaagatat tgccacttac tattgt                                96

<210> SEQ ID NO 19
<211> LENGTH: 13
<212> TYPE: PRT
<213> ORGANISM: Artificial sequence
<220> FEATURE:
<223> OTHER INFORMATION: CDR3 of E12 light chain

<400> SEQUENCE: 19

Gln Gln Tyr Ile Lys Leu Pro Tyr Thr Phe Gly Gly Gly
1               5                   10

<210> SEQ ID NO 20
<211> LENGTH: 39
<212> TYPE: DNA
<213> ORGANISM: Artificial sequence
<220> FEATURE:
<223> OTHER INFORMATION: CDR3 of E12 light chain

<400> SEQUENCE: 20
cagcagtata ttaagcttcc gtacacgttc ggaggggga                              39

<210> SEQ ID NO 21
<211> LENGTH: 30
<212> TYPE: PRT
<213> ORGANISM: Artificial sequence
<220> FEATURE:
<223> OTHER INFORMATION: FWR1 of E12 heavy chain

<400> SEQUENCE: 21

Glu Val Lys Leu Val Glu Ser Gly Gly Gly Leu Val Lys Pro Gly Gly
1               5                   10                  15

Ser Leu Lys Leu Ser Cys Val Gly Ser Gly Phe Ala Phe Ser
            20                  25                  30

<210> SEQ ID NO 22
<211> LENGTH: 90
<212> TYPE: DNA
<213> ORGANISM: Artificial sequence
<220> FEATURE:
<223> OTHER INFORMATION: FWR1 of E12 heavy chain

<400> SEQUENCE: 22

```
gaagtgaagc tggtggaatc tgggggaggc ttagtgaaac ctggagggtc cctgaaactc    60
tcctgtgtgg gctctggatt cgctttcagt                                     90
```

<210> SEQ ID NO 23
<211> LENGTH: 5
<212> TYPE: PRT
<213> ORGANISM: Artificial sequence
<220> FEATURE:
<223> OTHER INFORMATION: CDR1 of E12 heavy chain

<400> SEQUENCE: 23

Thr Tyr Asp Met Ser
1               5

<210> SEQ ID NO 24
<211> LENGTH: 15
<212> TYPE: DNA
<213> ORGANISM: Artificial sequence
<220> FEATURE:
<223> OTHER INFORMATION: CDR1 of E12 heavy chain

<400> SEQUENCE: 24

```
acctatgaca tgtct                                                     15
```

<210> SEQ ID NO 25
<211> LENGTH: 14
<212> TYPE: PRT
<213> ORGANISM: Artificial sequence
<220> FEATURE:
<223> OTHER INFORMATION: FWR2 of E12 heavy chain

<400> SEQUENCE: 25

Trp Val Arg Gln Thr Pro Glu Lys Arg Leu Glu Trp Val Ala
1               5                   10

<210> SEQ ID NO 26
<211> LENGTH: 42
<212> TYPE: DNA
<213> ORGANISM: Artificial sequence
<220> FEATURE:
<223> OTHER INFORMATION: FWR2 of E12 heavy chain

<400> SEQUENCE: 26

```
tgggttcgcc agactccgga gaagaggctg gagtgggtcg ct                       42
```

<210> SEQ ID NO 27
<211> LENGTH: 17
<212> TYPE: PRT
<213> ORGANISM: Artificial sequence
<220> FEATURE:
<223> OTHER INFORMATION: CDR2 of E12 heavy chain

<400> SEQUENCE: 27

Tyr Ile Ser Gly Gly Gly Gly Thr Thr Tyr Tyr Pro Gly Thr Leu Lys
1               5                   10                  15

Gly

<210> SEQ ID NO 28
<211> LENGTH: 51
<212> TYPE: DNA
<213> ORGANISM: Artificial sequence
<220> FEATURE:
<223> OTHER INFORMATION: CDR2 of E12 heavy chain

<400> SEQUENCE: 28
tatattagtg gtggtggtgg caccacctac tatccaggca ctttgaaggg c                51

<210> SEQ ID NO 29
<211> LENGTH: 32
<212> TYPE: PRT
<213> ORGANISM: Artificial sequence
<220> FEATURE:
<223> OTHER INFORMATION: FWR3 of E12 heavy chain

<400> SEQUENCE: 29

Arg Phe Thr Met Ser Arg Asp Asn Ala Lys Asn Thr Leu Tyr Leu Gln
1               5                   10                  15
Met Ser Ser Leu Lys Ser Glu Asp Thr Ala Met Tyr His Cys Ala Arg
            20                  25                  30

<210> SEQ ID NO 30
<211> LENGTH: 96
<212> TYPE: DNA
<213> ORGANISM: Artificial sequence
<220> FEATURE:
<223> OTHER INFORMATION: FWR3 of E12 heavy chain

<400> SEQUENCE: 30
cgattcacca tgtccagaga caatgccaag aacaccctgt acctgcaaat gagtagtctg     60
aagtctgagg acacagccat gtatcactgt gcaaga                              96

<210> SEQ ID NO 31
<211> LENGTH: 22
<212> TYPE: PRT
<213> ORGANISM: Artificial sequence
<220> FEATURE:
<223> OTHER INFORMATION: CDR3 of E12 heavy chain

<400> SEQUENCE: 31

His Asn Tyr Arg Thr Pro Phe Ala Tyr Trp Gly Gln Gly Thr Leu Val
1               5                   10                  15
Thr Asp Ser Ser Asn His
            20

<210> SEQ ID NO 32
<211> LENGTH: 66
<212> TYPE: DNA
<213> ORGANISM: Artificial sequence
<220> FEATURE:
<223> OTHER INFORMATION: CDR3 of E12 heavy chain

<400> SEQUENCE: 32
cataactata ggactccgtt tgcttactgg ggccaaggga ctctggtcac tgactcttct     60
aaccat                                                                66

COMPOSITIONS AND METHODS FOR DIAGNOSING AND TREATING AN INFLAMMATION

CROSS REFERENCE TO RELATED APPLICATIONS

This application is a continuation of U.S. patent application Ser. No. 14/828,615, filed Aug. 18, 2015, which is a continuation of U.S. Pat. No. 9,145,460 filed Jun. 10, 2013, which is a division of U.S. Pat. No. 8,512,698, issued on Aug. 20, 2013, which is a National Phase of PCT Patent Application No. PCT/IL2006/001059 filed on Sep. 11, 2006, which is a continuation in part (CIP) of U.S. Pat. No. 8,017,113, issued on Sep. 13, 2011. The contents of the above applications are incorporated herein by reference.

SEQUENCE LISTING STATEMENT

The ASCII file, entitled 56550SequenceListing.txt, created on Jun. 9, 2013, comprising 11,661 bytes, submitted concurrently with the filing of this application is incorporated herein by reference.

FIELD AND BACKGROUND OF THE INVENTION

The present invention relates to antibodies, compositions and methods for diagnosing and treating inflammation. More particularly, the present invention relates to the use of anti scavenger receptor antibodies in treatment of an inflammatory response.

Inflammation is a physiological condition characterized in the acute form by the classical signs of pain, heat, redness, swelling and loss of function. Inflammation often accompanies diseases such as Multiple Sclerosis (MS), osteoarthritis, Inflammatory Bowl Disease (IBD) including Crohn's disease and ulcerative colitis, Rheumatoid Arthritis (RA), SLE, type I diabetes (IDDM), atherosclerosis, encephalomyelitis, Alzheimer's disease, stroke, traumatic brain injury, Parkinson's disease, septic shock and others. In most cases, there is no effective cure for inflammation associated with such disease and existing treatments are palliative and largely fail to control the underlying causes of tissue degradation.

Scavenger receptors (SRs) are cell surface proteins, which are typically found on macrophages and bind various types of chemically modified lipoproteins (1-3), such as low-density lipoprotein (LDL). This family of trans-membrane receptors which are highly varied in structure are involved in receptor-mediated endocytosis, phagocytosis of apoptotic cells and bacteria, as well as in cell adhesion [Peiser L. et al., Curr. Opin. Immun 14(1):123-128, 2002]. Since the massive receptor-mediated uptake of cholesterol from modified LDL can convert cultured macrophages into cholesteryl ester-filled foam cells, similar to those found in atherosclerotic plaques, it has been postulated that these receptors also function in deposition of LDL cholesterol of macrophages in artery walls during the initial stages of atherosclerotic plaque formation [1].

Scavenger receptors (SRs) are termed as such since they mediate the binding of remarkably wide variety of polyanionic ligands [e.g., modified proteins, sulfated polysaccharides and certain polynucleotides [1, 3, 4]. This property led to the hypothesis that these receptors form a part of an in innate immune response by serving as pattern recognition receptors that bind a wide variety of pathogen components [2-5].

SR-B1 (also referred to as SR-BI or CLA-I) is a macrophage scavenger molecule and a receptor for high-density lipoprotein (HDL) [2, 3, 6, 7] that mediates cholesterol uptake from cells [Rigotti A. et al., Curr. Opin. Lipidol., 8:181-8, 1997; Rigotti A. et al., Proc. Natl. Acad. Sci., 94:12610-5, 1997]. SR-B1 can also serve as a receptor for non-HDL lipoproteins and appears to play an important role in reverse cholesterol transport. In vivo experiments showed that this receptor is important for HDL metabolism in mice, and for the metabolism of LDL and HDL cholesterol in humans [Stang H. et al., J. Biol. Chem. 274:32692-8, 1999; Swarnakar S. et al., J. Biol. Chem. 274:29733-9, 1999]. Studies involving the manipulation of SR-B1 gene expression in mice, indicate that its expression protects against atherosclerosis [Kozarsky K. F., and Krieger M., Curr. Opin. Lipidol. 10:491-7., 1999; Ueda Y. et al., J. Biol. Chem. 275:20368-73, 2000; Acton S. L. et al., Mol. Med. Today 5:518-24., 1999]. It was also suggested that HDL and particularly its protein fraction Apo-A1 affect the in vitro production of pro-inflammatory mediators by macrophages (8). Among mediators derived from macrophages that propagate inflammation are interleukin 12 (IL-12), TNF-α and possibly IL-6 whereas, TGF-β and IL-10 have predominantly anti-inflammatory effects [Kiefer R. et al., Prog. Neurobiol. 64(2):109-27, 2001].

PCT Publication No. WO 2004/041179 teaches targeting of scavenger receptor SR-B1 (Cla-I) for the treatment of infectious diseases associated with invasion of foreign antigens such as bacterial or viral antigens (e.g., infection, sepsis and associated inflammation). This is based on the discovery that peptides with an amphipathic helical motif block cellular uptake of LPS (lipopolysaccharide) and proinflammatory responses induced by LPS, LTA (lipoteichoic acid) and bacterial cpn60 (Chaperonin 60) and amyloid peptides in vitro. Thus the inventors of PCT Publication No. WO 2004/041179 conclude that agents with an amphipathic motif targeting SR-BI (scavenger receptor class B type I) could potentially be used to treat sepsis, bacterial and viral infections and inflammatory diseases where LPS, LTA, viral envelope proteins, and/or heat shock proteins contribute to pathogenesis.

WO 2004/041179 does not suggest the above-described agents for the favourable treatment of autoimmune diseases (which are not associated with foreign pathogenic agents such as LPS, nor with amyloid) such as IBD. Nor does the art teach the use of SR-B1 specific antibody sequences having an anti-inflammatory activity activity for the treatment of inflammatory diseases in general and autoimmune diseases in particular, such as multiple sclerosis.

There is thus, a widely recognized need for and it would be highly advantageous to have novel agents and methods using same for targeting SR-B1 and treating autoimmune diseases.

SUMMARY OF THE INVENTION

According to one aspect of the present invention there is provided an isolated polypeptide comprising an antigen recognition domain capable of specifically binding a human scavenger receptor, wherein the antigen recognition domain comprises at least three CDR amino acid sequences selected from the group consisting of SEQ ID NO: 11, 15, 19, 23, 27 and 31.

According to another aspect of the present invention there is provided an isolated polypeptide comprising an antigen recognition domain capable of specifically binding a human scavenger receptor, wherein the antigen recognition domain comprises CDR amino acid sequences as set forth in SEQ ID NO: 11, 15, 19, 23, 27 and 31.

According to yet another aspect of the present invention there is provided an isolated polynucleotide comprising a nucleic acid sequence encoding the polypeptide.

According to still another aspect of the present invention there is provided a pharmaceutical composition comprising as an active ingredient the polypeptide.

According to an additional aspect of the present invention there is provided a method of reducing inflammation in a subject in need thereof, the method comprising administering to the subject a therapeutically effective amount of the polypeptide, thereby reducing the inflammation in the subject.

According to yet an additional aspect of the present invention there is provided use of the polypeptide for the manufacture of a medicament identified for treating IBD.

According to still an additional aspect of the present invention there is provided use of the polypeptide for the manufacture of a medicament identified for treating multiple sclerosis.

According to a further aspect of the present invention there is provided use of the polypeptide for the manufacture of a medicament identified for treating an autoimmune disease.

The present invention successfully addresses the shortcomings of the presently known configurations by providing novel compositions and methods containing same for diagnosing and treating an inflammatory response.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4 is a graph depicting the effect of E12 (closed squares), control isotype matching antibody (circles) or no treatment on ongoing EAE in mice induced with such, as determined by reduction in EAE score;

FIGS. 5a-c are bar graphs depicting the effect of E12 (pink) or control antibodies (grey) on cytokine secretion from spleen cells of 19 day EAE-induced mice. FIG. 5a—IL-4. FIG. 5b—IL-12. FIG. 5c—IL-10;

FIGS. 6a-f are photographs showing IL-10 immunostaining of Lumbar spinal cord sections from EAE induced mice (19 days of disease onset) subjected to no treatment (FIG. 6a), or treated with E12 (FIG. 6b), or isotype matching control antibody (FIG. 6c). FIGS. 6a-c shows staining with biotinylated E12 for presence of scavenger receptor expressing cells. FIGS. 6d-f shows staining with anti IL-10 antibody. Anti-SR-BI therapy reduces the histological score of EAE;

FIGS. 8a-i show representative immuno-histological sections obtained at day 12 of disease onset from control rats suffering from TNBS induced IBD (FIGS. 8a-c), rats suffering form TNBS induced IBD that were subjected to repeated administration of isotype matched control IgG (FIGS. 8d-f) in comparison to diseased rats treated with mAb E12 (FIGS. 8g-i). FIGS. 8a, d and g are stained with mAb ED1 (macrophages bio-marker); FIGS. 8b, e and h are stained with anti CD3 (T cell bio-marker) and FIGS. 8 c, f and I are stained with an anti IL-10 mAb.

DESCRIPTION OF THE PREFERRED EMBODIMENTS

Figure 1:
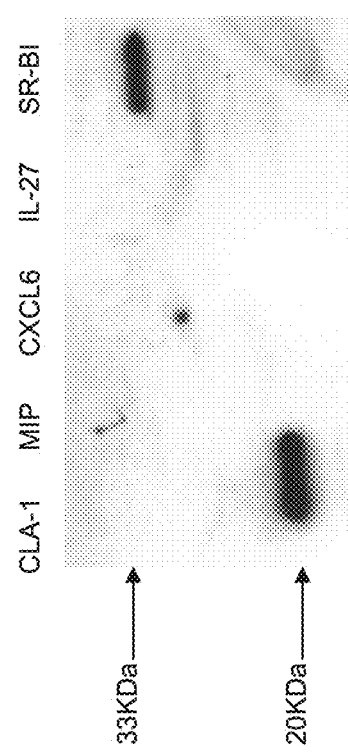
FIG. 1 is a photograph depicting cross-reactivity of monoclonal anti SR-B1 antibody, E12, with human and mouse orthologs. Recombinant proteins were resolved on SDS-PAGE and transferred to nitrocellulose membrane. The membrane was subjected to E12.

The present invention is of compositions and methods which can be used for the treatment of inflammation. Specifically, the present invention relates to the use of anti scavenger receptor antibodies in treating inflammatory response.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases and disorders which have significant inflammatory components are ubiquitous. Skin disorders, bowel disorders, certain degenerative neurological disorders, arthritis, autoimmune diseases and other illnesses afflict many patients. The factors underlying these disorders are varied and include infectious agents, autoimmune factors, dietary or environmental factors and genetic factors. In the majority of cases, the causative elements have not been defined and many of the key pathophysiological components have not been elucidated. Accordingly, treatment options for the majority of these diseases is suboptimal.

The present inventor has previously shown that the immune system can selectively generate autoimmunity to chemokines and other proinflammatory mediators when such a response is beneficial for the host [9, 10, 11, 12, 14, 15]. For example, patients suffering from rheumatoid arthritis (RA) but not osteoarthritis (OA) have significant levels of autoantibodies directed to TNF-α, and therapies that neutralize the function of TNF-α suppress RA but not OA. Studies conducted by the present inventor have shown that selective amplification of these beneficial antibodies by targeted DNA vaccines provided protective immunity in experimental models (9, 10, 11, 12, 14, 15). The present inventor have further shown that subjects suffering from inflammatory disease exhibit elevated levels of autoantibodies to scavenger receptor (SR) and showed that DNA vaccination against SR-B1 can prevent such diseases by altering the cytokine profile produced by macrophages from pro-inflammatory cytokines to anti-inflammatory cytokines (see WO2004/080385).

It is now reported that the present inventor also developed, through laborious experimentations and screening a novel therapeutic anti-SR-B1 monoclonal antibody, E12, which is capable of altering the cytokine profile and inflammatory activities of macrophages. This antibody which was sequenced is directed against a surface exposed epitope of the scavenger receptor (FIG. 1) and is cross-reactive to human CLA-I (human SR-B1) and also affects the cytokine profile and in vitro activities of human macrophages (a cell line) and as such can be used as a valuable therapeutic and diagnostic tool (see Example 1 and FIGS. 1-3). This antibody was also shown effective in suppressing ongoing EAE and TNBS induced IBD (see FIGS. 4-8). Immunohistological analysis clearly showed that in both diseases anti SR-BI therapy altered the cytokine production of invading leukocytes, at the autoimmune site, into high IL-10 producing cells. This may explain significant therapeutic effect of this antibody in these diseases. Immunohistological analysis of CNS sections using anti SR-BI mAb also showed that SR-BI positive leukocytes enter the site of inflammation (so far detected only for EAE). Thus, it is suggested that anti SR-BI antibodies described herein affect the cytokine profile and inflammatory functions of inflammatory leukocytes entering the autoimmune site, and thereby the function and polarization of autoimmune T cells there.

These findings suggest that the present antibody can be used for targeting scavenger receptor and for treatment of inflammatory diseases, especially IBD and multiple sclerosis.

Thus according to one aspect of the present invention there is provided an isolated polypeptide comprising an antigen recognition domain capable of specifically binding a human scavenger receptor, wherein said antigen recognition domain comprises at least three CDR amino acid sequences selected at least 90% homologous to the group consisting of SEQ ID NOs.: 11, 15, 19, 23, 27 and 31.

According to one embodiment of this aspect of the present invention the polypeptide comprises the CDR amino acid sequences are as set forth in SEQ ID NOs.: 11, 15, 19, 23, 27 and 31.

Preferably, the polypeptide is an antibody. More preferably the antibody is capable of eliciting an anti-inflammatory activity. As used herein "an anti-inflammatory activity" refers to any reduction in immune cell inflammatory activity, such as reduction in pro-inflammatory cytokine (such as TNF-α, IL-1 and IL-12) secretion preferably accompanied by induction of anti-inflammatory cytokine (e.g., IL-10, IL-4 and TGF-b) secretion.

The term "antibody" refers to whole antibody molecules as well as functional fragments thereof, such as Fab, F(ab')$_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Methods of generating antibodies are well known in the art. Purification of serum immunoglobulin antibodies (polyclonal antisera) or reactive portions thereof can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods of generating and isolating monoclonal antibodies are well known in the art, as summarized for example in reviews such as Tramontano and Schloeder, Methods in Enzymology 178, 551-568, 1989. A recombinant scavenger receptor polypeptide may be used to generate antibodies in vitro (see Example 6 of the Examples section which follows). In general, a suitable host animal is immunized with the recombinant polypeptide. Advantageously, the animal host used is a mouse of an inbred strain. Animals are typically immunized with a mixture comprising a solution of the recombinant polypeptide in a physiologically acceptable vehicle, and any suitable adjuvant, which achieves an enhanced immune response to the immunogen. By way of example, the primary immunization conveniently may be accomplished with a mixture of a solution of the recombinant polypeptide and Freund's complete adjuvant, said mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the polypeptide can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice. Hybridomas that secrete antibodies that recognize the recombinant polypeptide are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art (see also Example 6 of the Examples section). Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Antibodies of the present invention can be encoded from isolated polynucleotides which comprise nucleic acid sequences such as set forth in SEQ ID NOs. 12, 16, 20, 24, 28 and 32.

Polypeptides of the present invention can be synthesized using solid phase peptide synthesis procedures which are well known in the art and further described by John Morrow Stewart and Janis Dillaha Young, Solid Phase Peptide Syntheses (2nd Ed., Pierce Chemical Company, 1984). Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the polypeptides are desired, they can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

As mentioned, the polypeptides (also referred to herein as agents) of the present invention may be used for reducing or treating an inflammatory response (i.e., inflammation) in a subject.

As used herein the term "treating" refers to preventing, curing, reversing, attenuating, alleviating, minimizing, suppressing or halting the deleterious effects of an inflammatory response.

As used herein the phrase "inflammatory response" refers to an immune response which results in inflammation, typically occurring as a result of injurious stimuli including infection, burns, trauma, neoplasia, autoimmune signals and exposure to chemicals, heat or cold or any other harmful stimulus. An inflammatory response according to the present invention refers to an acute phase response and a chronic inflammation.

As used herein the term "subject" refers to subject who may benefit from the present invention such as a mammal (e.g., canine, feline, ovine, porcine, equine, bovine, human), preferably a human subject.

The method of this aspect of the present invention is effected by providing to a subject in need thereof a therapeutically effective amount of the polypeptide of the present invention, thereby reducing the inflammatory response in the subject.

As used herein a "scavenger receptor" refers to a gene product (i.e., RNA or protein) of a scavenger receptor, which is known in the Art. Examples of scavenger receptors include but are not limited to class A scavenger receptors, class B scavenger receptors and class F scavenger receptors. The scavenger receptor is preferably one which is expressed and displayed by macrophages. Preferably, the scavenger receptor of the present invention is SR-BI, a member of the CD36 family, GenBank Accession No. NP_005496, also known as CLA-I or SR-B1.

Scavenger receptor activity refers to cell adhesion activity, transporter activity, apoptotic activity, lipid metabolism activity, signal transduction activity and/or preferably cytokine secretion activity.

An effector of a scavenger receptor refers to an endogenous molecule which up-regulates or activates scavenger receptor activity. For example, an effector can be a modified lipid (e.g., oxidized lipid, glycated lipid, alkylated lipid, nitrated lipid, acetylated lipid), which binds to the scavenger receptor and activates signaling therefrom.

The above-described agents can be provided to the subject per se, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch. The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use. The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated. Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

A number of diseases and conditions, which typically cause inflammatory response in individuals can be treated using the methodology described hereinabove. Examples of such diseases and conditions are summarized infra.

Inflammatory Diseases—

Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrin Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan.

18; 91 (2):437), systemic diseases, systemic autoimmune diseases, systemic lupus erythematosus (*Datta* SK., Lupus 1998; 7 (9):591), glandular diseases, glandular autoimmune diseases, pancreatic diseases, pancreatic autoimmune diseases, Type 1 diabetes (Castano L. and Eisenbarth G S. Ann Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus *foliaceus.*

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus *foliaceus.*

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (*Nobile*-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed.

(1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Therapeutic Monoclonal Human Anti SR-BI Antibody

A monoclonal human anti SR-B1 antibody was produced for therapeutic use.

Materials and Methods

SR-B1 Encoding Plasmids:

DNA encoding human SR-B1 (CLA-I) was amplified using sense primer: 5' CCATGGGCTGCTCCGCCAAA 3' (SEQ ID NO: 6), and anti-sense primer: 5' CTACAGTTTT-GCTTCCTGCAG 3' (SEQ ID NO: 7) The above described reaction mixture was subjected to an amplification program of 1 min at 95° C., 1 min at 55° C. and 1 min at 72° C. for 25 cycles, generating 1.53 kb DNA fragment of SEQ ID NO:8 (*Homo sapiens* encoding SR-B1 mRNA, nucleotides 70-1599 from accession number: Z22555). After PCR reaction, the mixture was loaded onto a 5% polyacrylamide gel in TAE buffer. PCR product was gel-purified, cloned into a pUC57/T vector (T-cloning kit K1212; MBI Fermentas, Vilnius, Lithuania) and then used to transform *E. coli* cells. Clones were then sequenced (Sequenase version 2; Upstate Biotechnology, Cleveland, Ohio) and transferred into a pcDNA3 vector (Invitrogen, San Diego, Calif.). Large-scale preparation of plasmid DNA was conducted using Mega prep (Qiagen, Chatsworth, Calif.).

Cells:

HEK293 (ATCC) were transfected with human SR-B1 as described before [Scarselli E, et al., EMBO J. 21(19):5017-25, 2002]. Expression was verified by FACS analysis as described before [Scarselli E, et al., EMBO J. 21(19):5017-25, 2002].

Production of Monoclonal Human Anti SR-B1 Antibody:

Human anti SR-B1 monoclonal antibodies were produced according to one of the two following protocols:

Protocol I

C57/B6 mice were subsequently immunized (3 weekly immunizations) with the human SR-B1 (SEQ ID NO:8) encoding DNA plasmid. Two weeks after the last administration, these mice were subjected to active induction of EAE. Spleen cells were obtained for production of monoclonal antibodies two weeks later with SP2 cells (ATCC) as a fusion partner as described before (E. Harlow & D. Lane, Antibodies, Cold Spring Harbor Laboratory Press, 1998). Screening of positive hybridoma was done in two steps of selection. The first one selected positive antibodies producing cells according to the ability to bind the recombinant SR-B1 over expressed by HEK293. Supernatant isolated from hybridoma clones (1000 wells) was then subjected to FACS analysis for their ability to bind SR-B1

Protocol II

The cloned human SR-B1 (SEQ ID NO:8), obtained as described above, was re-cloned into a pQE expression vector, expressed in *E. coli* (Qiagen) and then purified by an NI-NTA-supper flow affinity purification of 6×His proteins (Qiagen). After purification, the purity of the recombinant human SR-B1 was verified by gel electrophoresis followed by sequencing (N terminus) by the Technion's sequencing services unit (Technion, Haifa, Israel). This recombinant human SR-B1 was then injected into 10-weeks old BALB/C mice. First immunization was of 50 µg peptide emulsified in CFA [incomplete Freund's adjuvant (IFA) supplemented with 10 mg/ml heat-killed *Mycobacterium tuberculosis* H37Ra in oil; Difco Laboratories, Detroit, Mich.] at a total volume of 400 µl into the peritoneal cavity. Later on, in a 3 weeks interval these mice were administrated with 50 µg/400 µl or recombinant human SR-B1 emulsified in IFA (Difco Laboratories, Detroit, Mich.). Three weeks after the third interval mice were injected (intravenous) with 50 µg of recombinant human SR-B1 in 100 µl PBS. Three days later spleen cells were obtained and preparation of monoclonal antibodies was conducted as described above.

ELISA—

The indirect ELISA was used to screen hybridomas for antibodies against SR-BI, as follows. Ninety six-well microtiter plates (NUNC) were coated with 50 ng/ml of immuno (recombinant) SR-BI (SEQ ID NO: 8) in phosphate buffered saline (PBS) overnight at 4° C., followed by blocking with 200 µl of 5% BSA in PBS. Then 100 µl of hybridoma supernatants were added and incubated for 1 hr at room temperature (RT). The plates were washed 4 times with PBS containing 0.05% Tween 20 (PBS-T), and then supplemented with peroxidase-conjugated goat anti-mouse IgG antibody for 1 hr at RT, and washed 5 times with PBS-T. Then 100 µl of substrate solution 3,3',5,5'-tetramethyl Benzedrine liquid (ICN biomedical INC, Germany, TMB) were added. The reaction was stopped using 2.5M $H_2SO_4$ and the absorbance was read by an ELISA reader at a wavelength of 450 nm and background of 630 nm.

Cell Binding Assay—

HEK 293 cell line was stably transfected with pcDNA encoding SR-BI (pcSR-BI). Positive clones were selected using neomycin (G418). The positively isolated ELISA hybridoma clones (isolated as described above) were taken into the second screen. Ninety six well disposable flexible polyvinyl chloride microtitration plates (Dynatech laboratories, Virginia) were seeded with $1*10^6$ pcSR-BI-expressing HEK 293 cells. The cells were washed twice with PBS before 100 µl of hybridomas supernatants were added for 30 minutes on ice. Following 3 washes with PBS, peroxidase-conjugated goat anti-mouse IgG antibody was added for additional 20 min on ice. Following 3 washes with PBS 100 µl of substrate solution (TMB) was added. The reaction was stopped using 2.5M $H_2SO_4$. After a short centrifugation, the reaction was transferred into a clean well and the absorbance was read by an ELISA reader at a wavelength of 450 nm and background of 630 nm.

Example 2

In Vitro Characterization of Anti SR-BI Therapeutic Antibodies

Human SR-B1 cross-reactive antibodies (with CLA-I) generated as described in Example 1 according to protocol 2 were in-vitro screened and characterized. The most successful antibody obtained was E12, which was further in-vitro characterized as further described hereinbelow.

Materials and Experimental Procedures

Immunoblot Analysis—

For single-label immunohistochemistry, standard methodology was used whereby sections were incubated with primary antibodies (1:100), followed by incubation with secondary antibodies (1:100). Mouse IgG and rabbit polyclonal IgG were used as control antibodies Isotype Analysis—

Isotype analysis was done using Serotec kit www.serotec.com.

Culture of Peritoneal Macrophages—

Resident macrophages were obtained from a peritoneal lavage with PBS. Elicited macrophages were harvested 5 days following i.p. injection of 3 ml of 3% Thioglycollate (TG, Difco, Livonia, Mich.). Peritoneal exudate cells were washed, re-suspended in RPMI 1640 medium supplemented with 10% FCS, 1% penicillin, 1% streptomycin, and incubated in 24 flat-bottom plates ($10^6$ cells per well in 1 ml) for overnight at 37° C. Nonadherent cells were then removed by vigorous washing (three times), and macrophages monolayers were incubated for 1-10 days in antibiotic-free RPMI containing 10% FCS. Fresh medium was provided every 3 days.

IL-10 Production by Macrophage Culture

The peritoneal macrophages generated as described above were treated with mAb E12 with or without 0.5 μg/ml LPS (Sigma) for 24 hr at 37° C. Supernatants from either treated or untreated macrophages were assayed for the presence of IL-10 or using immunoenzimatic ELISA kits (Biolegend).

Nitrite Production by Macrophage Culture—

Nitrite formation measurement was done according as described by [Katakura, T., M. Miyazaki, M. Kobayashi, D. N. Herndon, and F. Suzuki. (2004). CCL17 and IL-10 as effectors that enable alternatively activated macrophages to inhibit the generation of classically activated macrophages. J Immunol 172:1407]. Peritoneal macrophages ($1*10^6$/ml) were seeded in 24-well plates as describe above. Following treatment with LPS and/or mAb E12 the supernatant was taken and NO production was assayed by measuring the accumulation of nitrite in the culture medium by Griess reaction using Griess reagent system kit (Promega). Briefly: an equal volume of Griess reagent (Sulfanilamide Solution) and macrophage supernatants was incubated for 10 min at RT in a dark room. An equal volume of N-1-napthylethyl-enediamine dihydrochloride (NED) was then added for 10 min. An ELISA reader measured the absorbance at 550 nm Nitrite concentration was determined using $NaNO_2$ as a standard.

Results

Isotype analysis of E12 revealed it to be IgG1. The purified E12 was reacted with a nitrocellulose membrane containing various recombinant proteins. As shown in FIG. 1, mAb E12 cross reacted with SR-BI and CLA-1 but not with MIP, CXCL6 or IL-27. These results indicate that the antibody specifically recognizes scavenger B1 receptor in a cross-species dependent manner and is capable of recognizing the denatured form of the protein indicating that it is directed against an exposed epitope of the native protein, as further demonstrated by its ability to neautralize SR-B1 activity.

Figure 2:
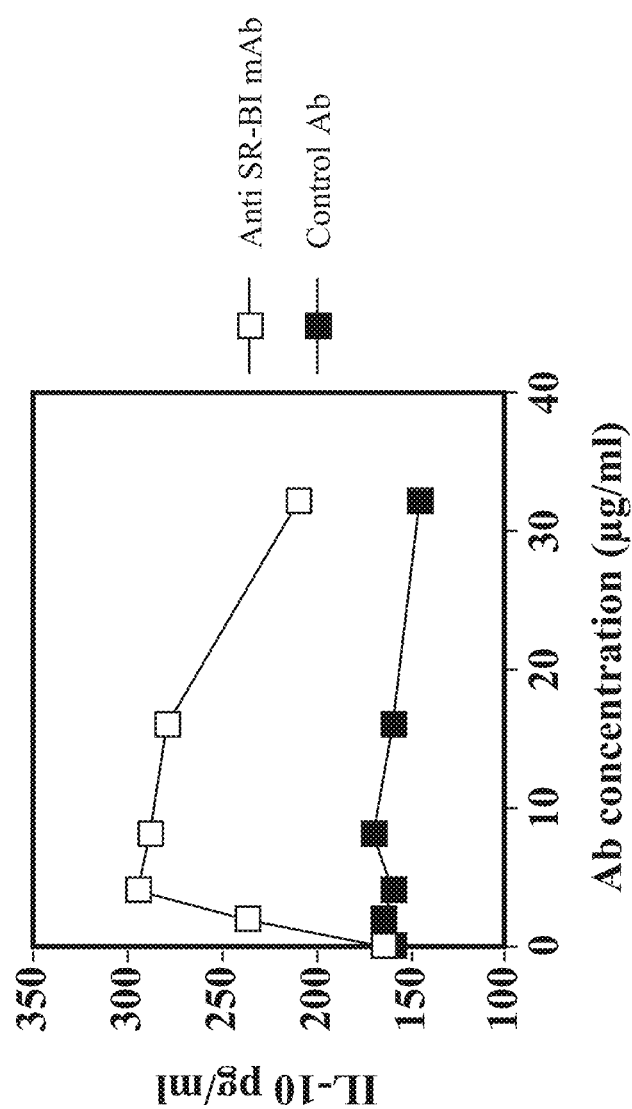
FIG. 2 is a graph depicting dose-dependent induction of IL-10 secretion from cultured peritoneal macrophages treated with E12.

The ability of E12 to elicit anti-inflammatory activity, was in vitro assayed on cultured peritoneal macrophages. As shown in FIG. 2 cultured peritoneal macrophages treated for 24 hours with 0.5 μg/ml LPS and with mAb E12, or with isotype matched control IgG, produced significantly higher IL-10 in the presence of increasing amounts of E12 than compared to control treated cells.

Figure 3:
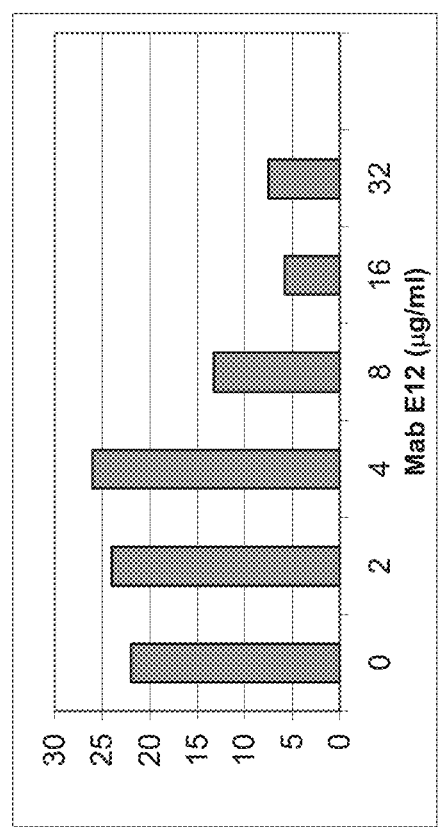
FIG. 3 is a bar graph depicting dose-dependent suppression of NO levels in cultured peritoneal macrophages treated with E12.

These results were substantiated when following NO levels in the presence of E12 antibody and LPS (0.5 μg/ml). As shown in FIG. 3, mAb E12 suppressed NO synthesis (as determined by nitrite levels) by peritoneal macrophages in a dose dependent manner Control matched isotypes had no effect of NO levels.

The variable regions of E12 heavy chain (VH) and light chain (VK) were sequenced and their CDR composition determined SEQ ID NO: 9 and 10 show the amino acid and nucleic acid sequences of framework 1 (FWR1) of E12 light chain, respectively. SEQ ID NO: 11 and 12 show the amino acid and nucleic acid sequences of CDR1 of E12 light chain, respectively. SEQ ID NO: 13 and 14 show the amino acid and nucleic acid sequences of framework 2 (FWR2) of E12 light chain, respectively. SEQ ID NO: 15 and 16 show the amino acid and nucleic acid sequences of CDR2 of E12 light chain, respectively. SEQ ID NO: 17 and 18 show the amino acid and nucleic acid sequences of framework 3 (FWR3) of E12 light chain, respectively. SEQ ID NO: 19 and 20 show the amino acid and nucleic acid sequences of CDR3 of E12 light chain, respectively.

SEQ ID NO: 21 and 22 show the amino acid and nucleic acid sequences of framework 1 (FWR1) of E12 heavy chain, respectively. SEQ ID NO: 23 and 24 show the amino acid and nucleic acid sequences of CDR1 of E12 heavy chain, respectively. SEQ ID NO: 25 and 26 show the amino acid and nucleic acid sequences of framework 2 (FWR2) of E12 heavy chain, respectively. SEQ ID NO: 27 and 28 show the amino acid and nucleic acid sequences of CDR2 of E12 heavy chain, respectively. SEQ ID NO: 29 and 30 show the amino acid and nucleic acid sequences of framework 3 (FWR3) of E12 heavy chain, respectively. SEQ ID NO: 31 and 32 show the amino acid and nucleic acid sequences of CDR3 of E12 heavy chain, respectively.

Example 3

A Monoclonal Antibody to SR-B1 is Capable of Suppressing Ongoing EAE and IBD

The monoclonal antibody generated as taught in Example 1 above was shown highly effective in suppressing ongoing EAE and TNBS induced IBD, as further described hereinbelow.

Materials and Methods

Induction of EAE in Mice and Suppression of the Ongoing Disease with mAb to SR-B1—

A group of 18 C57BL/6 mice was subjected to MOGp35-55 induced EAE. At the onset of disease (day 13) these mice were separated into three equally sick groups. On this day and on days 15 and 17 these groups were intraveneously administered with 500 μg E12 mAb, isotype matched human IgG (IgG1), or PBS and followed for clinical manifestation of disease (FIG. 4) by an observer blind to the experimental protocol.

Spinal Cord Histopathology—

Histological examination of H&E-stained sections of formalin-fixed, paraffin-embedded sections of the lower thoracic and lumbar regions of the spinal cord was performed. Each section was evaluated without knowledge of the treatment status of the animal. The following scale was used: 0, no mononuclear cell infiltration; 1, one to five perivascular lesions per section with minimal parenchymal infiltration; 2, five to 10 perivascular lesions per section with parenchymal infiltration; and 3, >10 perivascular lesions per section with extensive parenchymal infiltration. The mean histological score±SE was calculated for each treatment group Immunohistochemistry—

For single-label immunohistochemistry, standard methodology was used whereby sections were incubated with primary antibodies (1:100), followed by incubation with secondary antibodies (1:100). Mouse IgG and rabbit polyclonal IgG were used as control antibodies Induction of Experimental Colitis in Lewis Rats—

Experimental colitis was induced by intrarectal instillation of 250 µl of 125 mg/ml 2,4,6-trinitrobenzene sulfonic acid (TNBS) solution (Fluka, cat#92822) dissolved in 50% ethanol, using 8 cm neonate feeding tube as described before [Fiorucci, S. et al., Immunity, 17:769., 2002]. 24 hours post injection all rats developed bloody diarrhea and severe diarrhea in the next day, accompanied with continuous loss of weight.

Treatment Protocol for Antibody Transfer—

On days 6, 8 and 10 post induction of experimental colitis, 500 µg of mAb E12 was injected intravenously via a tail vein. Human IgG1 (Sigma) was used as a control antibody.

Sample Collection—

On day 12, the rats were killed under ketamine-xylasine anesthesia. The terminal colon was then stripped, gently washed with PBS, opened longitudinally and macroscopically evaluated according to a modification of the criteria described by Morris Gut (2004); 53; 99-107. Colonic injury was scored on a 0 (normal colon) to 5 (severe damage) scale, (see Table 2, below).

Colon Histopathology—

Tissues (terminal colon, mesentery lymph nodes and spleens) were fixed in 10% neutral buffered formalin and embedded in paraffin. Hematoxylin and eosin stained sections of the colon were evaluated histologically for four parameters: extent of ulceration, submucosal infiltration, crypt abscesses and wall thickening (see Table 3). The sum of all scores determined a rating of slight to severe colonic inflammation.

Immunohistochemistry—

Serial sections from formalin-fixed, paraffin-embedded specimens were deparaffinized and rehydrated in decreasing concentrations of ethyl alcohol. Tissue sections were incubated with fresh 3% $H_2O_2$ in methanol for 10 min and then washed with PBS. Sections were then treated by microwave for 15 min in 90° C. in citrate buffer and blocked with 10% donkey serum for 30 min Immunoistochemical analysis was carried out using primary antibodies against rat IL-10 (polyclonal goat anti rat IL-10, R&D), CD3 (mAb mouse anti rat, Pharmingen) and ED1 (mAb mouse anti rat, Serotec) over night at 4° C. in a humidified chamber. Biotinylated donkey anti goat or anti mouse IgG were used as secondary antibodies, followed by a streptavidin-horseradish peroxidase (Zymed). The reaction was developed using aminoethylcarbazole substrate kit (Zymed).

TABLE 2

Macroscopic assessment of colonic damage

| Macroscopic damage | Score |
|---|---|
| No damage | 0 |
| Hyperemia but no ulcers | 1 |
| Fibrosis but no ulcers | 2 |
| Ulceration/necrosis <1 cm | 3 |
| Ulceration/necrosis <2 cm | 4 |
| Ulceration/necrosis >2 cm | 5 |

TABLE 3

Microscopic assessment of colonic inflammation

| Histological appearance | Score |
|---|---|
| Extent of ulceration | |
| No ulcer | 0 |
| Small ulcers (<3 mm) | 1-2 |
| Large ulcers (>3 mm) | 3-5 |
| Submucosal infiltration | |
| None | 0 |
| Mild | 1 |
| Moderate | 2-3 |
| Severe | 4-5 |
| Crypt abscesses | |
| None | 0 |
| Rare | 1-2 |
| Diffuse | 3-5 |
| Wall thickness (µm) | |
| <470 | 0 |
| <600 | 1 |
| <700 | 2 |
| <800 | 3 |
| <900 | 4 |
| >900 | 5 |

Results

Anti SR-BI mAb Suppress Long-Term Ongoing EAE

Three groups of mice models of EAE displaying similar clinical manifestations were subjected to monoclonal antibody therapy and control treatments. As shown in FIG. 4, mice treated with PBS or control IgG continued to develop severe EAE, while those treated with the anti SR-BI mAb E12 went into fast remission without residual sign of disease (FIG. 4).

On day 19, spleen cells were isolated from representative mice of each group and cultured for 72 h with the target antigen with which disease was induced. Levels of IL-10, IL-12 (p40 subunit) and IL-4 were then recorded using commercially available ELISA kits. FIGS. 5a-c summarize the results of this experiment showing a marked elevation in IL-10 production (p<0.001), a significant elevation in IL-4 production (p<0.01) accompanied by a significant reduction in IL-12 production (p<0.01). These results are consistent with the in vitro properties of this antibody (see FIGS. 5a-c and may explain, at least in part the beneficial effect of this therapy (FIG. 4).

Spinal cord (lumbar spinal cord) sections obtained on day 19 from control EAE mice and from those subjected to IgG1 or E12 therapy (see FIG. 4) were subjected to an immunohistological analysis of the expression of SR-BI on leukocytes around high endothelial venules (HEV). FIGS. 6a-c show representative sections of untreated control EAE mice, EAE mice treated with E12 and EAE mice treated with control IgG1, respectively. In all sections of sick mice leukocytes entering the CNS highly expressed SR-BI. The reduction in the density of these cells in anti SR-BI treated mice could be explained, in part, by the reduced number of invading leukocytes resulting from the decrease in the inflammatory process (i.e. lower histological score).

Finally representative sections from these groups were subjected to immunohistological analysis of IL-10, using a commercially available anti IL-10 mAb. FIGS. 6d-f show representative sections of untreated control EAE mice, EAE mice treated with E12 and EAE mice treated with control IgG1, respectively. The elevation in IL-10 production in sections of mice treated with E12 is apparent compared to each of the control groups. These results support the above in-vitro results, substantiating the anti-inflammatory role of anti SR-B1 therapy.

Anti SR-BI mAb Suppresses Experimental Colitis

Similar analysis of the effect of anti-SR-B1 monoclonal antibodies on IBD was effected on a rat model of colotis. The following summarizes macroscopic and microscopic analyses on colitis induced rats (6 rats per group), as well as representative samples of histopathological analysis, followed by immunohistochemistry detection of ED1 positive cells (macrophages), CD3$^+$ T cells and IL-10 staining in all groups.

Table 4 below clearly shows that a significant reduction in macroscopic and microscopic scores of disease which is accompanied by a marked reduction in histopathological changes in the colon.

TABLE 4

|  | TNBS | TNBS control IgG | TNBS E12mAb |
|---|---|---|---|
| Mean macroscopic assessment | 4 ± 0.66 | 4.2 ± 0.66 | 2.66 ± 0.5* |
| Mean microscopic assessment | 15 ± 2 | 17.5 ± 2.2 | 6.5 ± 2** |

*p < 0.01,
**p < 0.001

Figure 7D:
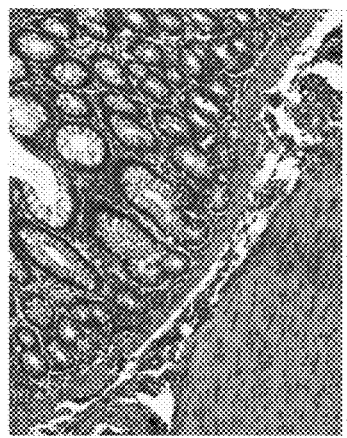
FIGS. 7a-e are photographs showing representative histological colon sections obtained at day 12 of disease onset from naïve rats (FIG. 7a), positive control rats suffering form TNBS induced IBD (FIG. 7b), rats suffering from TNBS induced IBD that were subjected to repeated administration of isotype matched control IgG (FIG. 7c) in comparison to those treated with mAb E12 (FIGS. 7d-e)
Figure 7E:
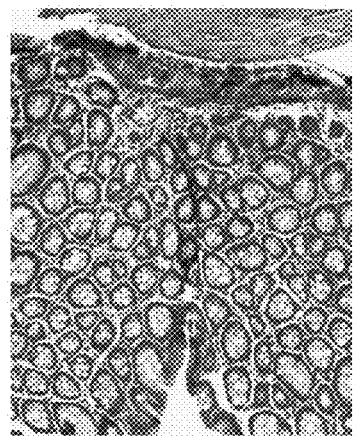
Figure 7A:
Figure 7B:
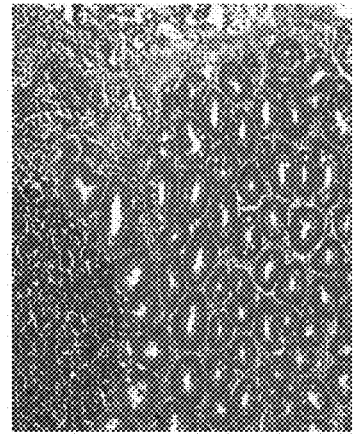
Figure 7C:

FIGS. 7a-e show representative histological colon sections obtained at day 12 of IBD onset from naïve rats (FIG. 7a), positive control rats suffering form TNBS induced IBD (FIG. 7b), rats suffering from TNBS induced IBD that were subjected to repeated administration of isotype matched control IgG (FIG. 7c) in comparison to those treated with mAb E12 (FIGS. 7d-e). As shown structural changes between E12 treated colon and control are evident. This may be explained by the shift in cytokine profile from pro-inflammatory (in control treated animals) to anti-inflammatory cytokines (in E12 treated animals) as shown in FIGS. 8a-i.

FIGS. 8a-c show sections of untreated IBD induced rats. Massive submucosal infiltration of macrophages (ED1$^+$) and both mucosal and submucosal infiltration of T cells (CD3+) are shown. IL-10 production was barely detected, mainly in the mucosa.

FIGS. 8d-f show sections of isotype matching control treated animals. Submucosal infiltration of macrophages (ED1+), mucosal infiltration of T cells (CD3+) and minor IL-10 production in the mucosa are detected.

FIGS. 8g-i show sections of E12 treated rats. Submucosal infiltration of macrophages (ED1+) in damaged areas is shown, and presence of macrophages in the lamina propria of unaffected areas is detected. CD3+ T cell infiltrate healthy mucosa, with marked IL-10 production at the mucosa.

REFERENCES CITED

Additional References are Cited in the Text

1. Brown M S, Goldstein J L. Lipoprotein metabolism in the macrophage: implications for cholesterol deposition in atherosclerosis. Annu Rev Biochem 1983; 52:223-61.
2. Krieger M. The other side of scavenger receptors: pattern recognition for host defense. Curr Opin Lipidol 1997; 8:275-80.
3. Krieger M, Herz J. Structures and functions of multiligand lipoprotein receptors: macrophage scavenger receptors and LDL receptor-related protein (LRP). Annu Rev Biochem 1994; 63:601-37.
4. Platt N, Gordon S. Is the class A macrophage scavenger receptor (SR-A) multifunctional?—The mouse's tale. J Clin Invest 2001; 108:649-54.
5. Janeway C A. Approaching the asymptote? Evolution and revolution in immunology. Cold Spring Harb. Symp. Quant. Biol. 1989; 54:1-13.
6. Acton S L, Scherer P E, Lodish H F, Krieger M. Expression cloning of SR-BI, a CD36-related class B scavenger receptor. J Biol Chem 1994; 269:21003-9.
7. Krieger M. Scavenger receptor class B type I is a multiligand HDL receptor that influences diverse physiologic systems. J Clin Invest 2001; 108:793-7.
8. Hyka N, Dayer J M, Modoux C, et al. Apolipoprotein A-I inhibits the production of interleukin-1β and tumor necrosis factor-α by blocking contact-mediated activation of monocytes by T lymphocytes. Blood 2001; 97:2381-9.
9. Youssef S, Maor G, Wildbaum G, Grabie N, Gour-Lavie A, Karin N. C—C chemokine-encoding DNA vaccines enhance breakdown of tolerance to their gene products and treat ongoing adjuvant arthritis. J Clin Invest 2000; 106:361-71.
10. Youssef S, Wildbaum G, Maor G, et al. Long-lasting protective immunity to experimental autoimmune encephalomyelitis following vaccination with naked DNA encoding C—C chemokines. J Immunol 1998; 161:3870-9.
11. Wildbaum G, Netzer N, Karin N. Plasmid DNA encoding IFN-γ-inducible protein 10 redirects antigen-specific T cell polarization and suppresses experimental autoimmune encephalomyelitis. J Immunol 2002; 168:5885-92.
12. Wildbaum G, Westermann J, Maor G, Karin N. A targeted DNA vaccine encoding fas ligand defines its dual role in the regulation of experimental autoimmune encephalomyelitis. J Clin Invest 2000; 106:671-9.
13. Wildbaum G, Youssef S, Karin N. A targeted DNA vaccine augments the natural immune response to self TNF-α and suppresses ongoing adjuvant arthritis. J Immunol 2000; 165:5860-6.
14. Wildbaum G, Karin N. Augmentation of natural immunity to a pro-inflammatory cytokine (TNF-α) by targeted DNA vaccine confers long-lasting resistance to experimental autoimmune encephalomyelitis. Gene Ther 1999; 6:1128-38.
15. Salomon I, Netzer N, Wildbaum G, Schif-Zuck S, Maor G, Karin N. Targeting the Function of IFN-γ-Inducible Protein 10 Suppresses Ongoing Adjuvant Arthritis. J Immunol 2002; 169:2685-93.
16. Sato Y, Roman M, Tighe H, et al Immunostimulatoey DNA sequences necessary for effective intradermal gene immunization. Science 1996; 273:352-357.
17. Raz E, Tighe H, Sato Y, et al. Preferential induction of a Th1 immune response and inhibition of specific IgE antibody formation by plasmid DNA immunization. Proc Natl Acad Sci USA 1996; 93:5141-5.
18. Hemmi H, Takeuchi O, Kawai T, et al. A Toll-like receptor recognizes bacterial DNA. Nature 2000; 408: 740-5.
19. Wen-Ming C, Xing Gong K, Zhi-Wei L, et al. DNA-PKcs Is Required for Activation of Innate Immunity by Immunostimulatory DNA. Cell 2000; 103:909-918.
20. Mendel I, Kerlero de Rosbo N, Ben-Nun A. A myelin oligodendrocyte glycoprotein peptide induces typical chronic experimental autoimmune encephalomyelitis in H-2b mice: fine specificity and T cell receptor V β expression of encephalitogenic T cells. European Journal of Immunology 1995; 25:1951-9.

21. Yednock T A, Cannon C, Fritz L C, Sanchez-Madrid F, Steinman L, Karin N. Prevention of experimental autoimmune encephalomyelitis by antibodies against α4β1 integrin. Nature 1992; 356:63-6.
22. Wildbaum G, Netzer N, Karin N. Tr1 cell-dependent active tolerance blunts the pathogenic effects of determinant spreading. J Clin Invest 2002; 110:701-10.
23. Husemann J, Silverstein S C. Expression of scavenger receptor class B, type I, by astrocytes and vascular smooth muscle cells in normal adult mouse and human brain and in Alzheimer's disease brain. Am J Pathol 2001; 158:825-32.
24. McRae B L, Kennedy M K, Tan L J, Dal Canto M C, Picha K S, Miller S D. Induction of active and adoptive relapsing experimental autoimmune encephalomyelitis (EAE) using an encephalitogenic epitope of proteolipid protein. Journal of Neuroimmunology 1992; 38:229-40.
25. Karin N, Binah O, Grabie N, et al. Short peptide-based tolerogens without self-antigenic or pathogenic activity reverse autoimmune disease. J Immunol 1998; 160:5188-94.

What is claimed is:

1. A method of treating multiple sclerosis (MS) in a subject in need thereof, the method comprising administering to said subject a therapeutically effective amount of an isolated polypeptide comprising an antigen recognition domain capable of specifically binding a human scavenger receptor, wherein said antigen recognition domain comprises CDR amino acid sequences as set forth in SEQ ID NOs.: 11, 15, 19, 23, 27 and 31.

* * * * *